United States Patent
Wang et al.

(10) Patent No.: US 7,356,521 B2
(45) Date of Patent: Apr. 8, 2008

(54) SYSTEM AND METHOD FOR AUTOMATIC MOLECULAR DIAGNOSIS OF ALS BASED ON BOOSTING CLASSIFICATION

(75) Inventors: Lu-yong Wang, Plainsboro, NJ (US); Amit Chakraborty, East Windsor, NJ (US); Dorin Comaniciu, Princeton Jct., NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 260 days.

(21) Appl. No.: 11/330,535

(22) Filed: Jan. 12, 2006

(65) Prior Publication Data

US 2006/0218109 A1 Sep. 28, 2006

Related U.S. Application Data

(60) Provisional application No. 60/644,154, filed on Jan. 14, 2005.

(51) Int. Cl.
*G06N 5/00* (2006.01)
(52) U.S. Cl. .......................................... 706/46; 706/25
(58) Field of Classification Search ................ 706/46, 706/47, 25; 702/22, 19; 435/6
See application file for complete search history.

(56) References Cited

U.S. PATENT DOCUMENTS

| 6,421,612 | B1 * | 7/2002 | Agrafiotis et al. ............. 702/19 |
| 6,675,104 | B2 * | 1/2004 | Paulse et al. .................. 702/22 |
| 6,905,827 | B2 * | 6/2005 | Wohlgemuth et al. ......... 435/6 |
| 7,026,121 | B1 * | 4/2006 | Wohlgemuth et al. ......... 435/6 |

OTHER PUBLICATIONS

Yoav Freund, et al., "A Short Introduction To Boosting," *Journal of Japanese Society for Artificial Intelligence*, 14(56): 771-780, Sep. 1999.
Yoav Freund, et al., "The Alternating Decision Tree Learning Algorithm".
Lu-Yong Wang, et al. "Molecular Diagnosis and Biomarker Identification On Seldi Proteomics Data By ADTBoost Method".

* cited by examiner

*Primary Examiner*—Wilbert L Starks, Jr.

(57) ABSTRACT

A method for diagnosing Amyotrophic lateral sclerosis includes providing surface-enhanced laser desorption/ionisation mass spectrometric (SELDI-MS) data of a plurality of proteins, said data obtained from a patient and comprising a plurality of peak values, and analysing said peak values with an alternating decision tree comprising a set of tests of said data peaks values and associated prediction values, wherein said data is predictive of depression if a sum of the prediction values of said tree is greater than 1.0.

21 Claims, 7 Drawing Sheets

1.1. Input: Sample: $S = \{(x_1, y_1), \ldots, (x_n, y_n)\}$, where $x_i \in X, y_i \in Y : \{-1, +1\}$
1.2. Initialize $W_1(i) = \frac{1}{n}$
1.3. For each $t=1,\ldots,T$:
1.4.     (1) Train the base lerner using distribution $W_i$
1.5.     (2) Get Weak hypothesis $h_t : X \rightarrow \{-1, +1\}$ with error
1.6. $$\varepsilon_t = \Pr_{i \sim D_t}[h_t(x_i) \neq y_i] = \sum_{i: h_t(x_i) \neq y_i} W_t(i)$$
1.7.     (3) Choose $\alpha_t = \frac{1}{2}\ln\left(\frac{1-\varepsilon_t}{\varepsilon_t}\right)$
1.8.     (4) Update:

$$W_{t+1}(i) = \frac{W_t(i)}{Z_t} \times \begin{cases} e^{-\alpha_t} & \text{if } h_t(x_i) = y_i \\ e^{\alpha_t} & \text{if } h_t(x_i) \neq y_i \end{cases} \quad \frac{W_t(i)e^{-\alpha_t y_i h_t(x_i)}}{Z_t},$$

where $Z_t$ is a normalization factor.

1.9. Output: Final hypothesis
$$H(x) = sign\left(\sum_{t=1}^{T} \alpha_t h_t(x)\right)$$

FIG. 1: The AdaBoost Algorithm

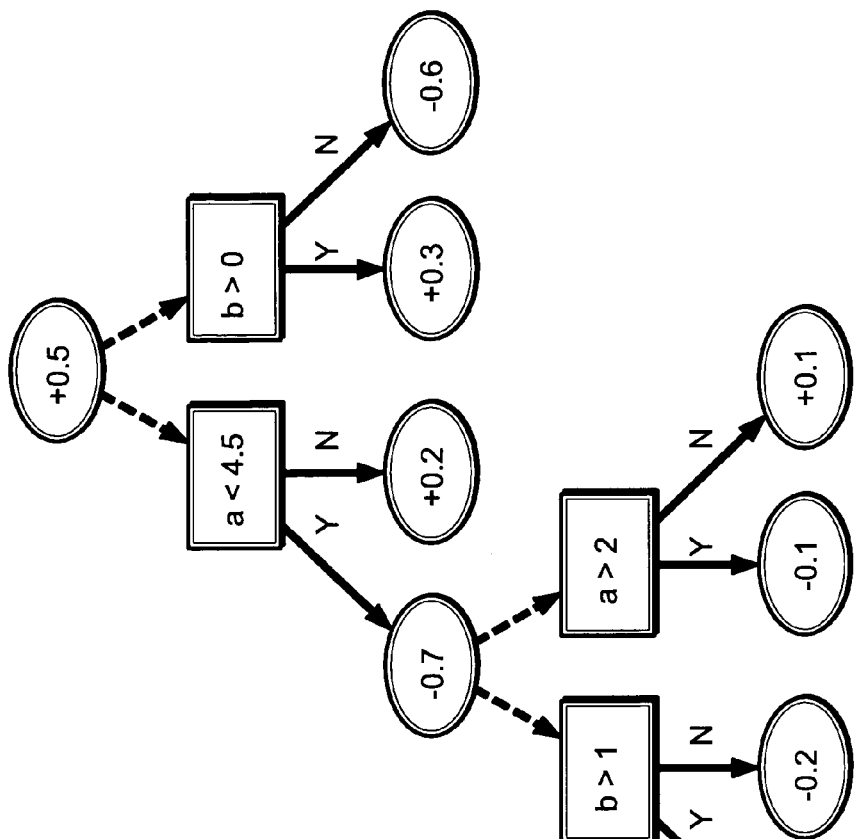
FIG. 2(c)
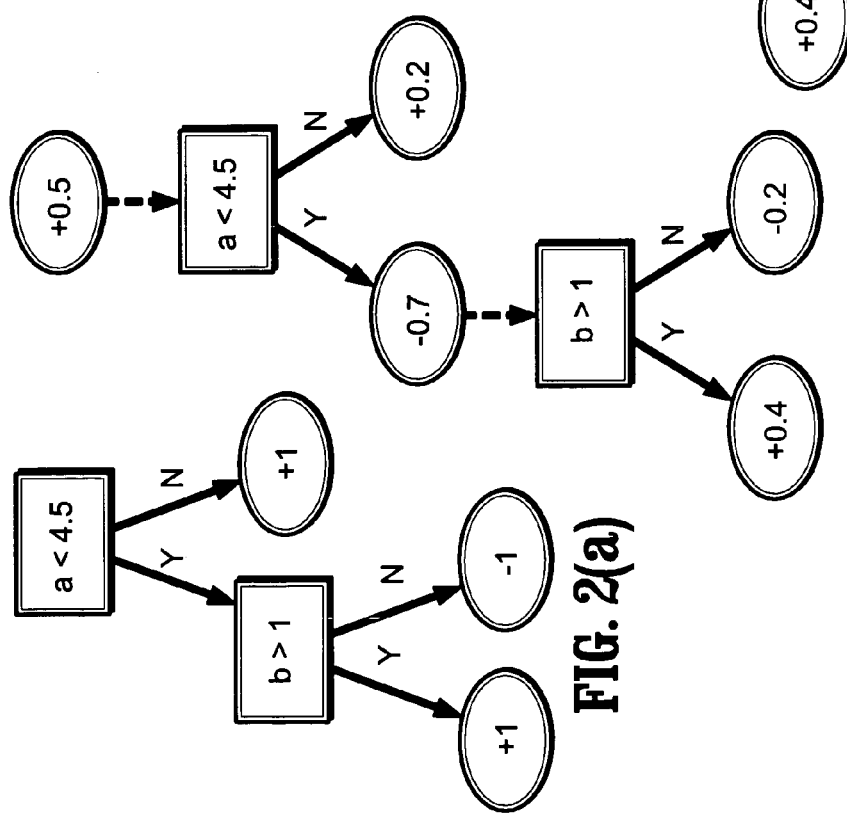
FIG. 2(b)
FIG. 2(a)

3.1. Input:
   Sample: $S = \{(x_1, y_1), \ldots, (x_n, y_n)\}$, where $x_i \in R^d, y_i \in Y : \{-1, +1\}$
   A set of base conditions $\Theta$.
3.2. Initialize set of preconditions: $P_1 = \{\mathbf{T}\}$
3.3. Initialize the weights $w_1(i)=1$, where $(1 \leq i \leq n)$.
3.4. Initialize the Alternative Decision Tree (ADT):

$$R_1 = \left\{ r_1 : \left( if(\mathbf{T}) then \left( if(\mathbf{T}) then \left( \frac{1}{2} \ln\left( \frac{W_+(\mathbf{T})}{W_-(\mathbf{T})} \right) \right) else(0) \right) else(0) \right) \right\}$$

3.5. For each $t=1,\ldots,T$:
3.6.     (1) Choose precondition $c_1 \in P_t$ and base condition $c_2 \in \Theta$ what minimize $Z_t(c_1,c_2)$ according to the equation:

$$Z_t(c_1,c_2) = 2\left(\sqrt{W_+(c_1 \wedge c_2)W_-(c_1 \wedge c_2)} + \sqrt{W_+(c_1 \wedge \neg c_2)W_-(c_1 \wedge \neg c_2)}\right) + W(\neg c_2),$$

3.7.     (2) Update ADT:

$$R_{t+1} = R_t \cup \left\{ r_{t+1} : \left( if(c_1) then \left( if(c_2) then \left( \frac{1}{2} \ln\left( \frac{W_+(c_1 \wedge c_2)}{W_-(c_1 \wedge c_2)} \right) \right) else \left( \frac{1}{2} \ln\left( \frac{W_+(c_1 \wedge \neg c_2)}{W_1(c_1 \wedge \neg c_2)} \right) \right) \right) else(0) \right) \right\}$$

3.8.     (3) Update precondition set: $P_{t+1} = P_t \cup \{c_1 \wedge c_2, c_1 \wedge \neg c_2\}$
3.9.     (4) Update weights: $w_{t+1}(i) = w_t(i)\exp(-y_i r_t(x_i))$
3.10. Output: ADT $R_{T+1}$.
3.11. Output classification: $class(\mathbf{x}) = sign\left(\sum_{t=1}^{T} r_t(\mathbf{x})\right)$.

FIG. 3: Boosting-based Alternating Decision Tree Algorithm

| WCX SELDI peaks (m/z) | 6690 | 13330 | 7661 | 4767 |
|---|---|---|---|---|
| $t$-test's p-value | 1.05e-09 | 0.006407 | 0.017395 | 0.019574 |

FIG. 4

|  | ALS patient | Control | Total |
|---|---|---|---|
| Test Positive | TP=28 | FP=8 | Total Positive=36 |
| Test Negative | FN=7 | TN=24 | Total Negative=31 |
| Total | ALS=35 | Control=32 | Grand Total=67 |
| Sensitivity = TP / (TP+FN) = 28/(28+8)=77.8%<br>Specificity = TN/(TN+FP) = 24/(24+7)=77.4% | | | |

FIG. 6

| | | | |
|---|---|---|---|
| If TRUE | then (if TRUE | then +0.075 else 0) | else 0 |
| If TRUE | then (if peak6690>=0.19 | then -0.331 else +4.293) | else 0 |
| If peak6690 >=0.19 | then (if peak22516>=0.06 | then -0.271 else +1.302) | else 0 |
| If peak22516>=0.06 | then (if peak23211>=0.06 | then +0.284 else -4.055) | else 0 |
| If peak23211>=0.06 | then (if peak1185 >=0.02 | then -0.294 else +4.043) | else 0 |

SYSTEM AND METHOD FOR AUTOMATIC MOLECULAR DIAGNOSIS OF ALS BASED ON BOOSTING CLASSIFICATION

CROSS REFERENCE TO RELATED UNITED STATES APPLICATIONS

This application claims priority from "An Automatic Molecular Diagnosis Approach Based on Boosting Classification and application in ALS disease", U.S. Provisional Application No. 60/644,154 of Wang, et al., filed Jan. 14, 2005, the contents of which are incorporated herein by reference.

TECHNICAL FIELD

This invention is directed to the automatic diagnosis of ALS (Amyotrophic lateral sclerosis) based on boosting classification of proteomic data.

DISCUSSION OF THE RELATED ART

As the human genome project is being finished, there is increasing need for bioinformatics to utilize the enormous amount of genomic information to devise computational procedures to solve the biomedical and clinical problems. In addition, modern biotechnology provides diverse means of high-throughout technology, such as microarray, SAGE and proteomics, for a bioinformatician to investigate the complex nature of human diseases.

Protein profiling in tissues and fluids in disease and pathological controls is frequently used for molecular-based diagnosis. Proteomic technologies will play an increasingly important role in molecular diagnosis, drug discovery and the practice of medicine in the post-genomic era, the first decade of the $21^{st}$ century. Proteomics is providing a better understanding of pathomechanisms of human diseases. Analysis of different levels of gene expression in healthy and diseased tissues by proteomic approaches is as important as the detection of mutations and polymorphisms at the genomic level and may be of more value in designing a rational therapy. Protein profiling in body tissues and fluids, in health as well as in disease, is the basis of the use of proteomic technologies for molecular diagnostics. Proteomics will play an important role in medicine of the future, which will be personalized and combine diagnostics with therapeutics.

Amyotrophic lateral sclerosis (ALS) is a progressive neurodegenerative disease that affects nerve cells in the brain and the spinal cord. Motor neurons reach from the brain to the spinal cord and from the spinal cord to the muscles throughout the body. The progressive degeneration of the motor neurons in ALS eventually leads to their death. When the motor neurons die, the ability of the brain to initiate and control muscle movement is lost. With voluntary muscle action progressively affected, patients in the later stages of the disease may become totally paralysed.

SUMMARY OF THE INVENTION

Exemplary embodiments of the invention as described herein generally include methods and systems for a boosting-based classification, for ALS diagnosis based on protein profiles obtained from mass spectrometry data. AdaBoost is one of the best classification methods known in statistical learning, to train classifier to predict the ALS disease from the normal controls. AdaBoost is a general method for improving the classification accuracy of any classification method. After each base learning iteration, misclassified training samples are adaptively given high weights in the next iteration. This forces the next base learner to focus on the misclassified training data. AdaBoost is utilized to learn the decision rules that make up an alternating decision tree. This combinatory algorithm, referred to herein as ADTboost, generates classification rules that simple and easy to interpret. It often identifies the discriminatory features, such as peaks in mass spectrometry data or genes in microarray data, which can be utilized as biomarkers for diagnostic purposes. In addition, ADTboost can provide a measure of prediction confidence. A method according to an embodiment of the invention is applied to SELDI MS (surface enhanced laser desorption ionization mass spectrometer) data of ALS patients and neurological controls to provide a molecular diagnosis method that can distinguish ALS disease from neurological controls. The resulting rules can be expressed in a simple and straightforward alternating decision tree format or conditional rule format, and identifies most discriminate peaks in SELDI data, which can be utilized as biomarkers for diagnosis.

A diagnosis method according to an embodiment of the invention can reduce the false positive rates, improve the prediction accuracy, provide a measure of confidence with the classification, and is robust to training error. A diagnosis method based on boosting classification is a useful and effective tool for diagnosis of neurological diseases like ALS. It can be applied to molecular diagnosis through microarray and proteomics data analysis and personalized medicine in a post-genomic era.

According to an aspect of the invention, there is provided a method for diagnosing Amyotrophic lateral sclerosis including providing surface-enhanced laser desorption/ionisation mass spectrometric (SELDI-MS) data of a plurality of proteins, said data obtained from a patient and comprising a plurality of peak values, and analysing said peak values with an alternating decision tree comprising a set of tests of said data peaks values and associated prediction values, wherein said data is predictive of depression if a sum of the prediction values of said tree is greater than 1.0.

According to a further aspect of the invention, the SELDI-MS peak values are identified from a univariant analysis of SELDI-MS data obtained from a plurality of patients, including patients diagnosed with Amyotrophic lateral sclerosis and control patients.

According to a further aspect of the invention, the univariant analysis comprises performing a standard t-test and a bonferroni correction.

According to a further aspect of the invention, the alternating decision tree is trained by applying a boosting algorithm to the SELDI-MS peak values identified from said plurality of patients.

According to a further aspect of the invention, the boosting algorithm includes providing a set of training examples $(x_1, y_1), \ldots, (x_m, y_m)$ where where $x_i \in R^d$ and $y_i \in \{-1,+1\}$, providing set of base conditions, initialising a set of preconditions to TRUE, initialising a set of weights for said training examples to a same initial value, initialising said alternating decision tree to a single rule with a precondition and base condition both set to TRUE, adding a new rule to said alternating decision tree, wherein said new rule comprises a base condition and a precondition that minimize a prediction function, updating said prediction set with a conjunction of said base condition and a negation of said base condition, and updating the set of weights based on prediction values of said new rule.

According to a further aspect of the invention, the prediction function $Z_t(c_1, c_2)$, wherein $c_1$ represents a precondition and $c_2$ represents a base condition, is defined by $$Z_t(c_1, c_2) = 2\left(\sqrt{W_+(c_1 \wedge c_2)W_-(c_1 \wedge c_2)} + \sqrt{W_+(c_1 \wedge \neg c_2)W_-(c_1 \wedge \neg c_2)}\right) + W(\neg c_2),$$

wherein $W_+(c)$, $W_-(c)$ denote the total weight of training set examples that satisfy c.

According to a further aspect of the invention, the prediction values of said new rule are $$\frac{1}{2}\ln\left(\frac{W_+(c_1 \wedge c_2)}{W_-(c_1 \wedge c_2)}\right) \text{ and } \frac{1}{2}\ln\left(\frac{W_+(c_1 \wedge \neg c_2)}{W_1(c_1 \wedge \neg c_2)}\right),$$

wherein $c_1$ represents a precondition and $c_2$ represents a base condition, and wherein $W_+(c)$, $W_-(c)$ denote the total weight of training set examples that satisfy c.

According to a further aspect of the invention, updating the set of weights comprises multiplying each said weight by $\exp(-y_i r(x_i))$, wherein $r(x_i)$ represents a value associated with training example $x_i$ by the new rule r, and, and $y_i \in \{-1, +1\}$.

According to a further aspect of the invention, the proteins are obtained from the cerebrospinal fluid of a patient.

According to a further aspect of the invention, the plurality of proteins were absorbed on a weak cationic exchanger chip.

According to another aspect of the invention, there is provided a program storage device readable by a computer, tangibly embodying a program of instructions executable by the computer to perform the method steps for diagnosing Amyotrophic lateral sclerosis

BRIEF DESCRIPTION OF THE DRAWINGS

FIG. 1 presents pseudocode of an exemplary AdaBoost algorithm, according to an embodiment of the invention.

FIGS. 2(a)-(c) depict several tree-based classifiers, according to an embodiment of the invention.

FIG. 3 presents pseudocode of an exemplary boosting alternating decision tree algorithm, according to an embodiment of the invention.

FIG. 4 is a table of results of univariant analysis of WCX SELDI 30 peaks between 36 ALS patients and 31 neurological controls, according to an embodiment of the invention.

FIG. 6 is a table of results of WCX SELDI diagnosis by AdaBoost, according to an embodiment of the invention.

DETAILED DESCRIPTION OF THE PREFERRED EMBODIMENTS

Figures 5A, 5B:
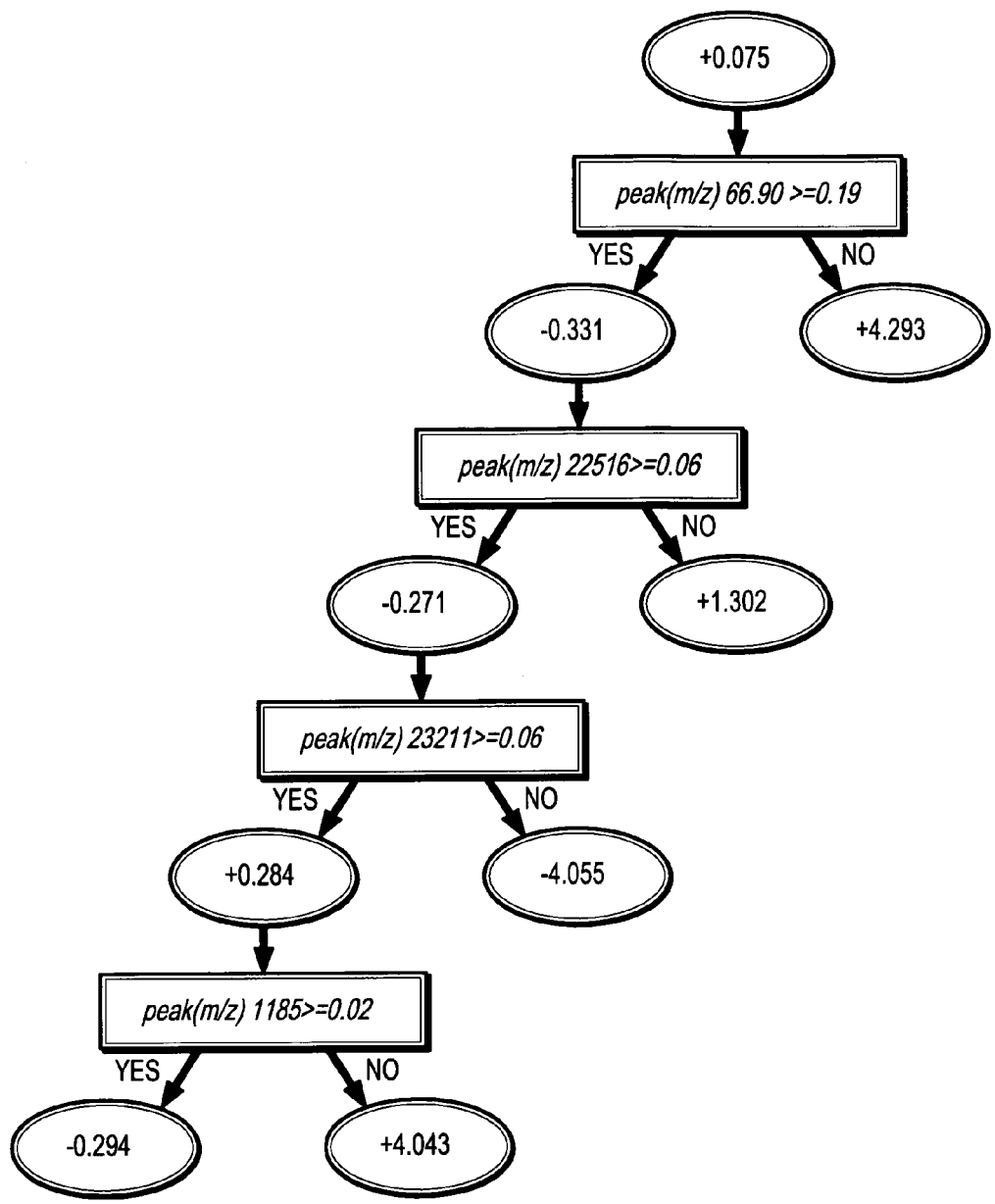
FIGS. 5(a)-(b) depict exemplary classifiers in an alternating-tree format from 5 round AdaBoost training and the corresponding rules, according to an embodiment of the invention.

Exemplary embodiments of the invention as described herein generally include systems and methods for a new diagnostic method based on boosting to improve classification accuracy of ALS disease data obtained from different SELDI MS (surface enhanced laser desorption ionization mass spectrometer) experimental procedures. A method according to an embodiment of the invention generates classification rules, which are simple and easy to interpret, identifies most discriminate features, which can be utilized as biomarkers for diagnostic purpose, and provides a measure of prediction confidence. Cross-validation and ROC analysis results indicated that good prediction capacity was obtained based on SELDI results through WCX procedure, although SAX2 and IMAC SELDI procedures did not provide sufficient discriminate information for ALS patients.

Boosting is a general method for improving the accuracy of any given learning algorithm. AdaBoost solved many practical difficulties of earlier boosting methods. AdaBoost is a boosting algorithm in that it can efficiently convert a weak learning algorithm, which can always generate a hypothesis with a weak edge for any distribution, into a strong learning algorithm, which can generate a hypothesis with an arbitrarily low error rate, given sufficient data. After each base learning iteration, misclassified training samples are adaptively given high weights in the next iteration. This forces the next base learner to focus on the misclassified training data. According to an embodiment of the invention, AdaBoost is utilized to learn decision rules comprising an alternating decision tree. This combinatory algorithm generates classification rules that provide most discriminatory features, such as peaks in mass spectrometry data, which can be utilized as biomarkers for diagnostic purposes. AdaBoost can also provide a measure of prediction confidence.

Pseudocode for AdaBoost is presented in FIG. 1. Referring to the figure, the algorithm at step 1.1 takes as input a training set $(x_1, y_1), \ldots, (x_m, y_m)$ where each $x_i$ belongs to some domain or instance space, and each label $y_i$ is in some label set Y. For expository purposes, it can without limitation be assumed that $Y = \{-1, +1\}$, although extensions to the multiclass case will also be disclosed. A main idea of the algorithm is to maintain a distribution or set of weights over the training set. The weight of this distribution on training example i on round t is denoted $W_t(i)$. Initially, at step 1.2, all weights are set equally. AdaBoost then calls a given weak or base learning algorithm repeatedly in a series of rounds $t = 1, \ldots, T$ at steps 1.3 and 1.4. On each round, the weights of incorrectly classified examples are increased so that the weak learner is forced to focus on the hard examples in the training set. At last, all the weak hypothesises are combined into a single strong hypothesis using a weighted majority vote schema.

The weak learner's job is to find, at step 1.5, a weak hypothesis $h_1: X \to \{-1, +1\}$ appropriate for the distribution $W_t$. At step 1.6, the goodness of a weak hypothesis is measured by its error $\epsilon_t$:

$$\varepsilon_t = Pr_{i \sim D_t}[h_t(x_i) \neq y_i] = \sum_{i: h_t(x_i) \neq y_i} W_t(i).$$

Notice that the error is measured with respect to the distribution $W_t$ on which the weak learner was trained. In practice, the weak learner can be any algorithm that can use the weights $W_t$ on the training examples. Alternatively, when this is not possible, a subset of the training examples can be sampled according to $W_t$, and these (unweighted) resampled examples can be used to train the weak learner.

Once the weak hypothesis $h_t$ has been received, AdaBoost chooses, at step 1.7, a parameter $\alpha_t$ that measures the importance that is assigned to $h_t$. Note that $\alpha_t \geq 0$ if $\epsilon_t \leq \frac{1}{2}$, (which we can assume without loss of generality), and that $\alpha_t$ gets larger as $\epsilon_t$ gets smaller.

The distribution $W_t$ is next updated at step 1.8 using the rule shown in the figure. The effect of this rule is to increase the weight of examples misclassified by $h_t$, and to decrease the weight of correctly classified examples. Thus, the weight tends to concentrate on "hard" examples. The final hypothesis H, which is output at step 1.9, is a weighted majority vote of the T weak hypotheses where $\alpha_t$ is the weight assigned to $h_t$.

AdaBoost and its analysis can be extended to handle weak hypotheses which output real-valued or confidence-rated predictions. That is, for each instance x, the weak hypothesis $h_t$ outputs a prediction $h_t(x) \in \Re$ whose sign is the predicted label (−1 or +1) and whose magnitude $|h_t(x)|$ gives a measure of "confidence" in the prediction. For expository purposes, however, exemplary, non-limiting embodiments of the invention focus on the case of binary ({−1, +1}) valued weak-hypothesis predictions. Many real-world learning problems, however, are multiclass with more than two possible classes, and there are several methods known in the art of extending AdaBoost to the multiclass case.

An important property of AdaBoost concerns its ability to reduce the training error. AdaBoost is also adaptive in that it adapts to the error rates of the individual weak hypotheses. This is the basis of its name: "Ada" is short for "adaptive."

Boosting decision tree learning algorithms can yield excellent classifiers. A simple decision tree is depicted in FIG. 2(*a*). This decision tree has two decision nodes and three prediction leaves. The tree defines a binary classification rule which maps instances of the form $(a,b) \in R^2$ into one of two classes denoted by −1 and +1. FIG. 2(*b*) illustrates a different representation of the same classification rule. In this representation each decision node is replaced by two nodes: (1) a prediction node, represented by an ellipse; and (2) a splitter node represented by a rectangle. The decision node is identical to that of FIG. 2(*a*), while the prediction node is now associated with a real valued number. Thus, an instance is mapped into a path along the tree from the root to one of the leaves. However, the classification that is associated with the path is not the label of the leaf, but rather the sign of the sum of the predictions along the path. For example, the classification of the instance a=b=0.5 is sign(0.5−0.7−0.2)=sign(−0.4)=−1. It is easy to check that the two trees define the same classification rule. It is also clear that many different trees of the second type can represent the same tree of the first type. The second representation is referred to as an "alternating tree" representation for the reason that it comprises alternating layers of prediction nodes and splitter nodes.

Alternating trees can be represented as a vote over simple prediction rules as follows. The tree in FIG. 2(*b*) can be considered as including a root prediction node and two units of three nodes each: a decision node, and the two prediction nodes that are its children. The classification rule described in FIG. 2(*b*) can now be rewritten as a weighted majority vote, by associating with each of the decision nodes a simple rule of the following form:

```
if(precondition) then
    if(condition) then output p1
    else output p2
else output 0
```

Specifically, the following two rules can be associated with the decision nodes in FIG. 2(*b*):

| r1(a,b)= | r2(a,b)= |
|---|---|
| if(always) then | if(a<4.5) then |
| if(a<4.5) then | if(b>1) then |
| output −0.7 | output +0.4 |
| else output +0.2 | else output −0.2 |
| else output 0 | else output 0 |

By combining these two rules with the constant prediction associated with the root node one can rewrite the classication rule represented by the decision tree as: sign(0.5+r1(a, b)+r2(a,b)). These rules are referred to as base rules.

This transformation enables one to represent any standard decision tree as a sum of base rules each of which corresponds to one of the decision nodes in the tree. In general, precondition is the conjunction of conditions that lead to a given decision node, condition is the decision associated with the node, and p1, p2 are the predictions associated with the two children of the decision node.

Standard decision trees can be generalized to general alternating decision trees to provide a more flexible semantics for representing classifiers. Standard decision trees define a partition of the instance space into disjoint regions. Most algorithms for learning decision trees work by iteratively splitting one of the partitions in two. Each part can be split at most once. In other words, only leaf nodes can be split. However, in general alternating decision trees each part can be split multiple times. Returning to the example, note that in the alternating tree depicted in FIG. 2(*b*), each predictor node has at most one splitter node attached to it. In FIG. 2(*c*), two splitter nodes were added to obtain an example of a general alternating tree.

A general alternating tree defines a classification rule as follows. An instance defines a set of paths in the alternating tree. When a path reaches a decision node, it continues with the child which corresponds to the outcome of the decision associated with the node. However, when reaching a prediction node, the path continues with all of the children of the node. More precisely, the path splits into a set of paths, each of which corresponds to one of the children of the prediction node. The union of all the paths reached in this way for a given instance is referred to as the "multi-path" associated with that instance. The sign of the sum of all the prediction nodes that are included in a multipath is the classification which the tree associates with the instance. As examples consider the following two instances: if a=1 and b=0.5 then the classification is sign(0.5+0.3−0.7−0.2+ 0.1)=sign(0.1)=+1; if a=5 and b=1 then the classification is sign(0.5+0.2+0.3)=sign(1.0)=+1. In both cases the classification is +1, however, the second prediction can be regarded as more confident then the first.

Formally, an alternating decision tree can be defined using the following notation and definitions, according to an embodiment of the invention. A base condition is a boolean predicate over instances. The symbol ˆ is used to denote conjunction (AND), ¬is used to denote negation (NOT), and T denotes the constant predicate that is always true. A set of base conditions is denoted by $\Theta$. A precondition is a conjunction of base conditions and negations of base conditions. A base rule r is a mapping from instances to real numbers which is defined in terms of a precondition $c_1$, a base condition $c_2$, and two real numbers a and b. The base rule maps each instance to a prediction that is defined to be a if $c_1 \wedge c_2$, b if $c_1 \wedge \neg c_2$, and 0 if $\neg c_1$. A base rule is denoted by r and r(x) denotes the real value that the rule associates with the instance x. With these definitions, an alternating decision tree comprises a set of base rules that maps instances to real numbers. The set of base rules must obey the two following two conditions:

(1) The set should include a base rule for which both the condition and the pre-condition are T. The a value of this rule is the prediction associated with the root of the tree.

(2) A base rule r with precondition d can be in the set only if the set includes a rule r' with precondition $c_1$ and base condition $c_2$ such that $d = c_1 \wedge c_2$ or $d = c_1 \wedge \neg c_2$. Here, d corresponds to the prediction node that is the direct parent of r.

The alternating tree maps each instance to a real valued prediction which is the sum of the predictions of the base rules in its set. The classification of an instance is the sign of the prediction.

Thus, alternating trees can be defined as a sum of simple base rules. The base rules generate predictions that can be any real valued number. As a result, it is a simple matter to apply any boosting algorithm to learning alternating decision trees from examples. The only consideration here is that the set of base rules (sometimes called "weak hypotheses") that are considered at each stage is not constant but increases as the tree is grown.

An alternating decision learning algorithm according to an embodiment of the invention is presented in FIG. 3. For expository purposes consider a set of inequality conditions that compares a single feature with a constant. This set of conditions is sufficiently restricted that it is feasible to enumerate all possible base rules that can be added to a given tree for a given training set. Referring to the figure, the algorithm at step 3.1 takes as input a training set $(x_1, y_1), \ldots, (x_m, y_m)$ where where $x_i \in R^d$ and $y_i \in \{-1, +1\}$, and a fixed set of base conditions denoted by $\Theta$. The base conditions are Boolean predicates comparing a single feature and a constant. The algorithm maintains two sets, a set of preconditions and a set of rules. The symbols $P_t$, $R_t$, respectively, correspond to these two sets on boosting iteration t. The initial precondition set is $P_1 = \{T\}$ at step 3.2. The algorithm associates a positive weight with each training example. Denote by $w_{i,t}$ the weight of example number i on boosting iteration t. The initial weights are set at step 3.3 as $W_{i,0} = 1$ for all examples $1 \leq i \leq m$. The set of rules comprising the tree is initialized at step 3.4 to a single base rule whose precondition and base condition are both T and whose first prediction value is $$a = \frac{1}{2} \ln\left(\frac{W_+(T)}{W_-(T)}\right).$$

The notation W(c) represents the total weight of the training examples which satisfy the predicate c, and $W_+(c)$, $W_-(c)$ denote the total weight of those examples that satisfy c and are labeled +1 or −1 respectively (i.e. $W(c) = W_+(c) + W_-(c)$). This rule represents the best constant prediction for the entire data set, and is placed at the root of the tree.

The tree is grown iteratively starting at step 3.5, with one base rule added at a time. At step 3.6, a precondition c1 and base condition c2 are selected that minimize the function $Z_t(c_1, c_2)$, as indicated in the figure. A new base rule is then added to the ADT at step 3.7 whose precondition is $c_1$, base condition is $c_2$, and whose two prediction values are $$a = \frac{1}{2} \ln\left(\frac{W_+(c_1 \wedge c_2)}{W_-(c_1 \wedge c_2)}\right) \text{ and } b = \frac{1}{2} \ln\left(\frac{W_+(c_1 \wedge \neg c_2)}{W_-(c_1 \wedge \neg c_2)}\right).$$

The added base rule corresponds to a subtree with a decision node as its root and two prediction nodes as the leaves. This subtree is added as a child of a predictor node which may or may not be a leaf node. At step 3.8, the precondition set is updated with the addition of conditions $c_1 \wedge c_2$ and $c_1 \wedge \neg c_2$ to the set. The weights of each training example are updated at step 3.9 according to the equation in the figure. Note that if $r(x_i) = 0$, the weight is unchanged, After T iterations, the ADT represented by the set of base rules $R_{T+1}$ is output at step 3.10. In this description, a criteria for stopping the boosting process has not been specified, or in other words, how to choose T, the maximum value for the iteration counter t. One exemplary, non-limiting technique for stopping the boosting uses a cross-validation.

When using the ADT to analyse and classify new data, the output, at step 3.11, is a classification rule that is the sign of the sum of the predictions of all of the base rules in $R_{T+1}$:

$$\text{class}(x) = \text{sign}\left(\sum_{t=1}^{T} r_t(x)\right).$$

The interpretation of alternating trees rests on the fact that the contribution of each decision node can be understood in isolation. Summing these contributions generates the prediction and the classification. After gleaning the meaning of each decision node in isolation one can analyze the interactions of the nodes. Parallel decision nodes represent little or no interaction. In contrast to the independence of parallel decision nodes, the significance of decision nodes in deeper level depends on the evaluation of their ancestral decision nodes. The decision-tree structure can represent dependences between indicators. The root of the tree is associated with an fixed (unconditional) contribution, which is the probability of a prediction before testing any feature value. All the contributions are summed in order to give the final prediction, and this prediction is thresholded to give the classification. This means that if the conditions given in the tree are tested serially, one accumulate evidence for or against the health of a person as one proceeds. If at some intermediate point during this process there is a sum whose absolute value is large, and the total contribution of all of the (untested) prediction nodes is small, then there is no need to continue the computation, as the current sign of the sum cannot change. The absolute value of the sum can be thought of as a measure of confidence of the classification.

The classification rules generated by combining an alternating tree with boosting, according to an embodiment of the invention, are often simpler and easier to interpret than those produced by previous learning techniques, and provide a measure of confidence.

A method according to an embodiment of the invention was used on SELDI MS data of ALS patients and neurological controls. The goal of this study was to identify specific sets of ALS diagnostic protein fingerprint based on WCX SELDI peak values in CSF to be used in the clinical setting. Univariant analysis was applied to 30 WCX SELDI peaks between 36 ALS patients and 31 neurological controls. The statistical procedure is composed of standard t-test and its bonferroni correction. FIG. 4 is a table of results of univariant analysis of these WCX SELDI 30 peaks between the 36 ALS patients and 31 neurological controls. As indicated in the table, the most significantly different WCX SELDI peak is 6690, which has a t-test p-value of 1.05% $10^{-9}$.

An AdaBoost algorithm according to an embodiment of the invention was used to learn decision rules constituting alternating decision trees and to generate classification rules while determining the most discriminative SELDI peaks. FIGS. 5(a)-(b) depict exemplary classifiers in an alternating-tree format from 5 round AdaBoost training: (a) alternating decision tree; and (b) the corresponding decision rules. As shown in the figures, the alternating decision tree was applied in this study to construct a classifier based on WCX protein species changes. The alternating decision tree for diagnosis prediction shown in FIG. 5(a) can also be transformed to sets of equivalent decision rules shown in FIG. 5(b), representing the classifier in a set of decision rules by 5 round training using AdaBoost.

Using this approach, the learning algorithm builds an alternating decision tree with a top down strategy based on SELDI MS peaks values from the ALS patients and neurological control cases used in this study. An alternating decision tree contains splitter nodes (associated with a test) and prediction nodes (associated with a value). At every boosting step, it selects and adds a new rule or equivalently a new unit consisting of a splitter node and two prediction nodes; and the weights are updated. The prediction values are chosen according to the ruleset update calculation formula in the algorithms depicted in FIG. 3. The initial prediction value, given as +0.075 in FIG. 5(a) at the root prediction node, is defined as $\frac{1}{2}\ln(W_+(T)/W_-(T))$, where $W_+(T)$ and $W_-(T)$ are, respectively, the sum of the weights of the positive (negative) examples that satisfy some condition. For the root prediction node, it is the initial "True" condition.

As shown in FIG. 5(a), a diagnostic prediction based on WCX SELDI peak values was indicated as a sign of the sum of the predictions along the related paths in the tree. The real value of this sum was used to determine the confidence in predicting an ALS diagnosis. For example, if two WCX SELDI peaks have m/z 6690 and m/z 22810 with a p-value value of 0.2449 and 0.0545, respectively, as is the case in one of the paths that terminates in the second node of FIG. 5(a), then the sum of the predictions is (+0.075-0.331+1.302)=+1.046. Because the sum is positive, the algorithm classified this as +1, which means that these SELDI peaks diagnostically predicted ALS with a high relative confidence (>1.0 in this case).

To evaluate AdaBoost diagnostic capacity, a 10-fold cross validation test was employed. Using the WCX SELDI MS peaks values acquired in this study, $\frac{9}{10}^{th}$ of the data were chosen from both positive and negative samples as training set, the remaining $\frac{1}{10}^{th}$ of the data was used for testing, and the process was iterated. The prediction results were benchmarked using 10-fold cross-validation, and the true positive (TP) hits, false positive (FP) hits, true negative (TN) hits and false negative (FN) hits were calculated. Using this approach, the prediction capacity of the AdaBoost classification method was evaluated for sensitivity and specificity (Sensitivity=TP/(TP+FN); Specificity=TN/(TN+FP)). FIG. 6 is a table of results of WCX SELDI diagnosis by AdaBoost. The results in the table are based on a 10 fold cross validation; the data is calculated from the ALS vs. Peskind Ctl cases using the WCX analysis procedure. As shown in the table, it was found that the sensitivity of this diagnostic method is 77.8% and the specificity is 77.4%.

Figure 7:
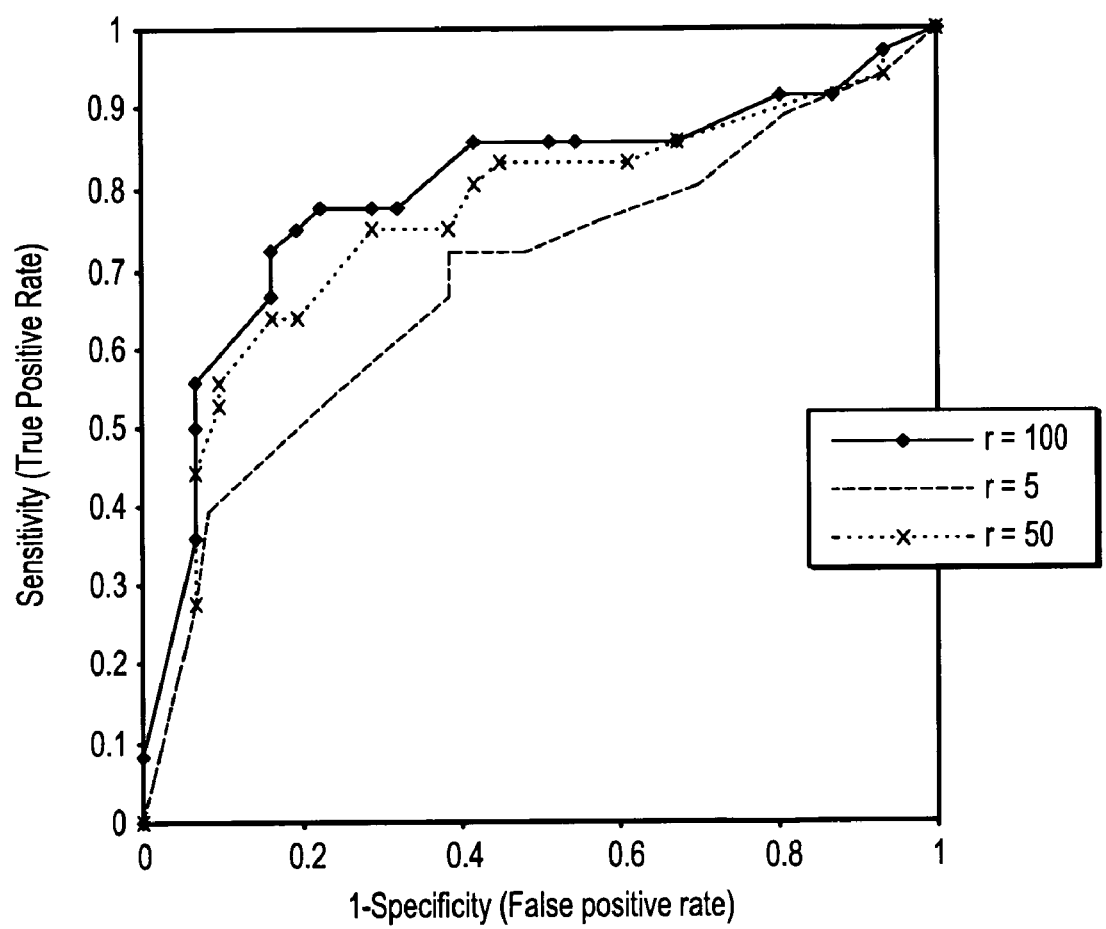
FIG. 7 is a graph of ROC curves based on an AdaBoost classification from the ALS vs Peskind control obtained by the WCX procedure, according to an embodiment of the invention.

An ROC (Receiver Operating Characteristic) curve was used to evaluate the diagnostic capacity of a method according to an embodiment of the invention. The ROC curve is a plot of the true positive rate (Sensitivity) against the false positive rate (1-specificity) for the different possible cut-off points of a diagnostic test, e.g. for ALS. FIG. 7 is a graph of ROC curves based on an AdaBoost classification from the ALS vs Peskind control obtained by the WCX procedure. The ROC curves are generated by changing the cut-off value of the classification algorithm, and depict the relationship between the true positive rate and false positive rate. The solid curve shows the classification results after 100 rounds of training, while the dotted curve shows the classification results after 50 rounds of training. The dashed curve indicates the classification results after 5 training rounds. Clearly, with more training the area under the ROC curve increases, i.e. the performance of the algorithm improves. The top four most significant SELDI peaks value are 6690 (the most important peak); 22516; 23211; 1185. The classification results were compared with the differential analysis (t-test with Bonferroni correction) for different peaks. The top differential peak is: m/z=6690, which has p-value of $1.05\%10^{-9}$ and p-value after bonferroni correction of $3.16\%10^{-8}$. Thus, the most important decision rule based on the boosting results is consistent with differential analysis.

It is to be understood that the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

Figure 8:
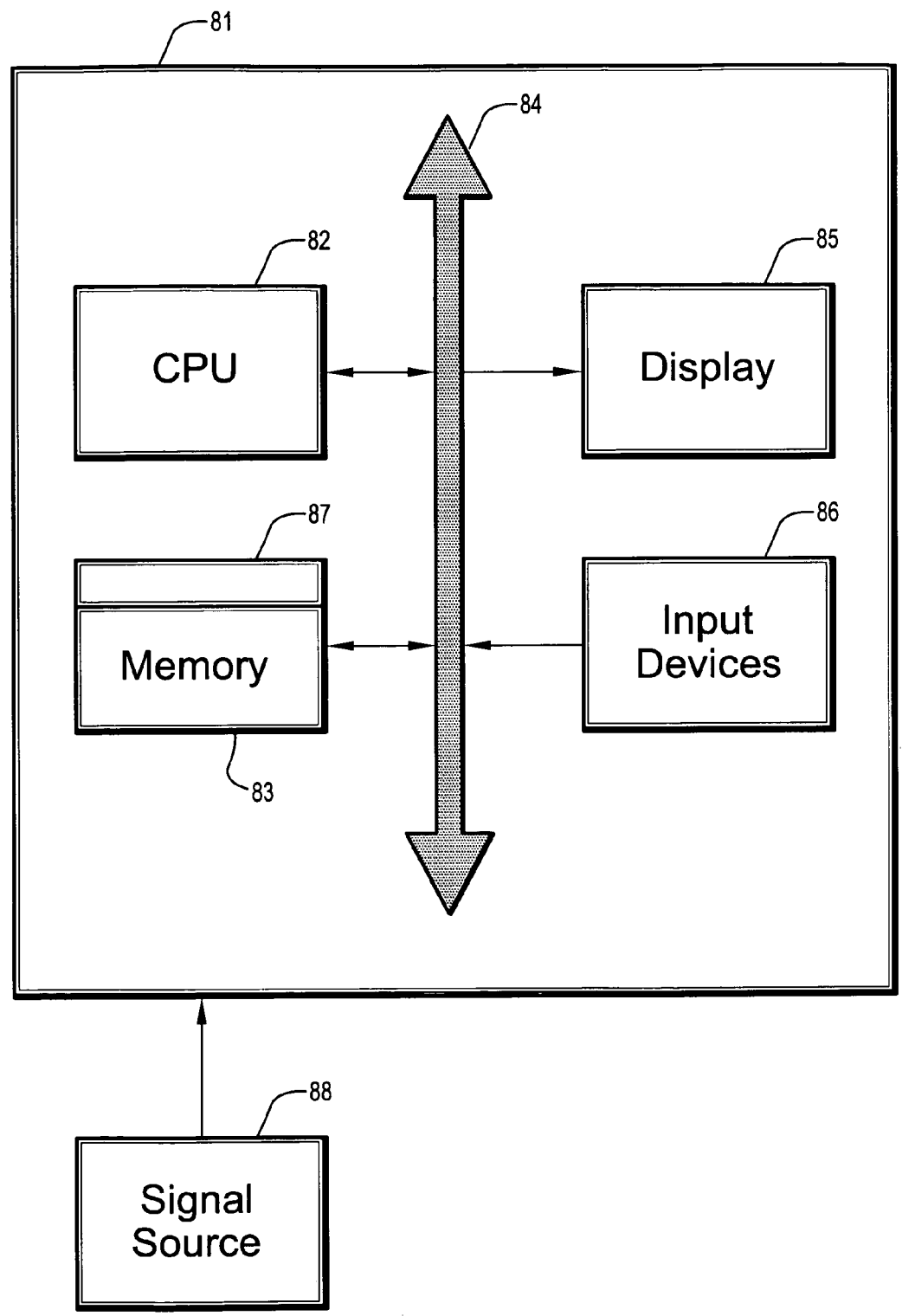
FIG. 8 is a block diagram of an exemplary computer system for implementing a boosting-based method for diagnosing ALS, according to an embodiment of the invention.

FIG. 8 is a block diagram of an exemplary computer system for implementing a boosting-based alternating decision tree classifier according to an embodiment of the invention. Referring now to FIG. 8, a computer system 81 for implementing the present invention can comprise, inter alia, a central processing unit (CPU) 82, a memory 83 and an input/output (I/O) interface 84. The computer system 81 is generally coupled through the I/O interface 84 to a display 85 and various input devices 86 such as a mouse and a keyboard. The support circuits can include circuits such as cache, power supplies, clock circuits, and a communication bus. The memory 83 can include random access memory (RAM), read only memory (ROM), disk drive, tape drive, etc., or a combinations thereof. The present invention can be implemented as a routine 87 that is stored in memory 83 and executed by the CPU 82 to process the signal from the signal source 88. As such, the computer system 81 is a general purpose computer system that becomes a specific purpose computer system when executing the routine 87 of the present invention.

The computer system 81 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While the present invention has been described in detail with reference to a preferred embodiment, those skilled in the art will appreciate that various modifications and substitutions can be made thereto without departing from the spirit and scope of the invention as set forth in the appended claims.

What is claimed is:

1. A method of diagnosing Amyotrophic lateral sclerosis comprising the steps of:
providing surface enhanced laser desorption/ionisation mass spectrometric (SELDI-MS) data of a plurality of proteins, said data obtained from a patient and comprising a plurality of peak values, wherein said SELDI-MS peak values are identified from a univariant analysis of SELDI-MS data obtained from a plurality of patients, including patients diagnosed with Amyotrophic lateral sclerosis and control patients; and
analysing said peak values with an alternating decision tree comprising a set of tests of said data peaks values and associated prediction values, wherein said data is predictive of Amyotropic lateral sclerosis if a sum of the prediction values of said tree is greater than 1.0.

2. The method of claim 1, wherein said univariant analysis comprises performing a standard t-test and a bonferroni correction.

3. The method of claim 1, wherein said alternating decision tree is trained by applying a boosting algorithm to the SELDI-MS peak values identified from said plurality of patients.

4. The method of claim 3, wherein said boosting algorithm comprises the steps of:
providing a set of training examples $(x_1, y_1), \ldots, (x_m, y_m)$ where where $x_i \in R^d$ and $y_i \in \{-1,+1\}$;
providing set of base conditions;
initialising a set of preconditions to TRUE;
initialising a set of weights for said training examples to a same initial value;
initialising said alternating decision tree to a single rule with a precondition and base condition both set to TRUE;
adding a new rule to said alternating decision tree, wherein said new rule comprises a base condition and a precondition that minimize a prediction function;
updating said prediction set with a conjunction of said base condition and a negation of said base condition; and
updating the set of weights based on prediction values of said new rule.

5. The method of claim 4, wherein said prediction function $Z_t(c_1, c_2)$, wherein $c_1$ represents a precondition and $c_2$ represents a base condition, is defined by $$Z_t(c_1, c_2) = 2\left(\sqrt{W_+(c_1 \wedge c_2)W_-(c_1 \wedge c_2)} + \sqrt{W_+(c_1 \wedge \neg c_2)W_-(c_1 \wedge \neg c_2)}\right) + W(\neg c_2),$$

wherein $W_+(c)$, $W_-(c)$ denote the total weight of training set examples that satisfy c.

6. The method of claim 4, wherein the prediction values of said new rule are $$\frac{1}{2}\ln\left(\frac{W_+(c_1 \wedge c_2)}{W_-(c_1 \wedge c_2)}\right) \text{ and } \frac{1}{2}\ln\left(\frac{W_+(c_1 \wedge \neg c_2)}{W_1(c_1 \wedge \neg c_2)}\right),$$

wherein $c_1$ represents a precondition and $c_2$ represents a base condition, and wherein $W_+(c)$, $W_-(c)$ denote the total weight of training set examples that satisfy c.

7. The method of claim 6, wherein updating the set of weights comprises multiplying each said weight by $\exp(-y_i r(x_i))$ wherein $r(x_i)$ represents a value associated with training example $x_i$ by the new rule r, and, and $y_i \in \{-1,+1\}$.

8. The method of claim 1, wherein said proteins are obtained from the cerebrospinal fluid of a patient.

9. The method of claim 1, wherein said plurality of proteins were absorbed on a weak cationic exchanger chip.

10. A method of diagnosing Amyotrophic lateral sclerosis comprising the steps of:
providing surface-enhanced laser desorption/ionisation mass spectrometric (SELDI-MS) data of a plurality of proteins, said data obtained from a plurality of patients, including patients diagnosed with Amyotrophic lateral sclerosis and control patients,
statistically analysing said data to identity significant peak values; and
training an alternating decision tree with a boosting algorithm using said significant peak values, wherein said alternating decision tree comprises a set of tests of said peaks values and associated prediction values.

11. The method of claim 10, further comprising using said alternating decision tree to analyze SELDI-MS data obtained from a new patient.

12. The method of claim 11, wherein an output of said alternating decision tree analysis of said new patient data is predictive of Amyotrophic lateral sclerosis if a sum of the prediction values of said tree is greater than 1.0.

13. A program storage device readable by a computer, tangibly embodying a program of instructions executable by the computer to perform the method steps for diagnosing Amyotrophic lateral sclerosis comprising the steps of:
providing surface-enhanced laser desorption/ionisation mass spectrometric (SELDI-MS) data of a plurality of proteins, said data obtained from a patient and comprising a plurality of peak values wherein said SELDI-MS peak values are identified from a univariant anal sis of SELDI-MS data obtained from a plurality of patients, including patients diagnosed with Amyotrophic lateral sclerosis and control patients; and
analysing said peak values with an alternating decision tree comprising a set of tests of said data peaks values and associated prediction values, wherein said data is predictive of Amyotrophic lateral sclerosis if a sum of the prediction values of said tree is greater than 1.0.

14. The computer readable program storage device of claim 13, wherein said univariant analysis comprises performing a standard t-test and a bonferroni correction.

15. The computer readable program storage device of claim 13, wherein said alternating decision tree is trained by applying a boosting algorithm to the SELDI-MS peak values identified from said plurality of patients.

16. The computer readable program storage device of claim 15, wherein said boosting algorithm comprises the steps of:
providing a set of training examples $(x_1, y_1), \ldots, (x_m, y_m)$ where where $x_i \in R^d$ and $y_i \in \{-1,+1\}$;
providing set of base conditions;
initialising a set of preconditions to TRUE;
initialising a set of weights for said training examples to a same initial value;
initialising said alternating decision tree to a single rule with a precondition and base condition both set to TRUE;

adding a new rule to said alternating decision tree, wherein said new rule comprises a base condition and a precondition that minimize a prediction function;

updating said prediction set with a conjunction of said base condition and a negation of said base condition; and updating the set of weights based on prediction values of said new rule.

17. The computer readable program storage device of claim 16, wherein said prediction function $Z_t(c_1, c_2)$, wherein $c_1$ represents a precondition and $c_2$ represents a base condition, is defined by $$Z_t(c_1, c_2) = 2\left(\sqrt{W_+(c_1 \wedge c_2)W_-(c_1 \wedge c_2)} + \sqrt{W_+(c_1 \wedge \neg c_2)W_-(c_1 \wedge \neg c_2)}\right) + W(\neg c_2),$$

wherein $W_+(c)$, $W_-(c)$ denote the total weight of training set examples that satisfy c.

18. The computer readable program storage device of claim 16, wherein the prediction values of said new rule are $$\frac{1}{2}\ln\left(\frac{W_+(c_1 \wedge c_2)}{W_-(c_1 \wedge c_2)}\right) \text{ and } \frac{1}{2}\ln\left(\frac{W_+(c_1 \wedge \neg c_2)}{W_1(c_1 \wedge \neg c_2)}\right),$$

wherein $c_1$ represents a precondition and $c_2$ represents a base condition, and wherein $W_+(c)$, $W_-(c)$ denote the total weight of training set examples that satisfy c.

19. The computer readable program storage device of claim 18, wherein updating the set of weights comprises multiplying each said weight by $y_i r(x_i)$, wherein $r(x_i)$ represents a value associated with training example $x_i$ by the new rule r, and, and $y_i \in \{-1, +1\}$.

20. The computer readable program storage device of claim 13, wherein said proteins are obtained from the cerebrospinal fluid of a patient.

21. The computer readable program storage device of claim 13, wherein said plurality of proteins were absorbed on a weak cationic exchanger chip.

* * * * *